United States Patent [19]

Tench et al.

[11] Patent Number: 5,466,349

[45] Date of Patent: Nov. 14, 1995

[54] POTENTIOMETRIC EVALUATION OF SUBSTRATE OXIDATION AND COATING POROSITY

[75] Inventors: D. Morgan Tench, Ventura; Petra V. Jambazian, Thousand Oaks, both of Calif.

[73] Assignee: Rockwell International Corporation, Seal Beach, Calif.

[21] Appl. No.: 369,844

[22] Filed: Jan. 6, 1995

[51] Int. Cl.⁶ .................................................. G01N 27/26
[52] U.S. Cl. .......................... 204/153.1; 204/153.11; 204/400; 204/404; 228/101; 228/103; 228/104
[58] Field of Search .......................... 204/153.1, 153.11, 204/404, 400; 228/101, 103, 104

[56] References Cited

U.S. PATENT DOCUMENTS

| | | | |
|---|---|---|---|
| 3,649,472 | 3/1972 | Morrissey et al. | 204/404 |
| 3,684,679 | 8/1972 | Smith et al. | 204/404 |
| 4,294,667 | 10/1981 | Yamamoto et al. | 204/404 |
| 4,495,558 | 1/1985 | Cath et al. | 204/153.1 |
| 5,262,022 | 11/1993 | Tench et al. | 204/153.1 |
| 5,324,399 | 6/1994 | Ludwig et al. | 204/153.1 |

OTHER PUBLICATIONS

Morrissey, R. J., "Electrolytic Determination of Porosity in Gold Electroplates," *J. Electrochem. Soc.*, vol. 117, No. 6, pp. 742–747 (Jun. 1970).

*Primary Examiner*—John Niebling
*Assistant Examiner*—Bruce F. Bell
*Attorney, Agent, or Firm*—John C. McFarren

[57] ABSTRACT

A fast, nondestructive, and easy to perform method of Potentiometric Evaluation of Substrate Oxidation ("PESO") is provided. A coated part to be analyzed is placed in contact with an electrolytic solution having a pH adjusted to provide an optimum oxide dissolution rate. The open circuit potential of the part is monitored as the substrate oxide dissolves in the electrolytic solution. The voltage typically changes as a function of time during oxide dissolution. When oxide dissolution is complete, the voltage reaches a steady value associated with active dissolution of the substrate metal and reduction processes on the coating. The electrolytic solution can be flowed or agitated to reduce concentration polarization, provide more meaningful voltage measurements, and minimize the time required for analysis. The time required to reach a steady-state voltage provides a measure of the amount of substrate oxide within pores in the coating. The final steady-state voltage level provides a measure of the relative areas of the coating and the exposed substrate, which relates to the porosity of the coating. The method is useful for evaluating the quality of coated parts by providing a quantitative measure of both substrate oxidation and coating porosity.

20 Claims, 2 Drawing Sheets

POTENTIOMETRIC EVALUATION OF SUBSTRATE OXIDATION AND COATING POROSITY

TECHNICAL FIELD

The present invention relates to methods of evaluating protective coatings and, in particular, to a method of potentiometric evaluation of substrate oxidation and coating porosity.

BACKGROUND OF THE INVENTION

Oxidation and corrosion of substrates through pores in protective coatings is a serious problem in the electronics and jewelry industries. Unfortunately, there are no currently available methods for detecting substrate oxidation, and coating porosity is difficult to evaluate by known methods, such as nitric acid or electrochemical spot testing, which are generally qualitative, destructive, and hard to perform. Vacuum surface analysis techniques do not provide unambiguous results for such measurements, and they are sufficiently expensive and cumbersome to preclude their routine use for most applications. Electrochemical techniques involving the passage of current, such as sequential electrochemical reduction analysis ("SERA") for solderability testing, have limited utility in analyzing substrate oxidation. A basic difficulty with current passage techniques for analyzing protective coatings is uncertainty regarding the area of the substrate exposed to the electrolyte solution. This area uncertainty translates to uncertainty in the applied current density, which introduces errors into the analytical results. For noble metal coatings, interfering reactions such as hydrogen evolution, for example, introduce additional errors in the results.

In Morrissey, R. J., "Electrolytic Determination of Porosity in Gold Electroplates," *J. Electrochem. Soc.*, Vol. 117, No. 6, pp. 742–47 (June 1970), it was shown that an absolute measure of porosity in terms of the area ratio of the substrate and coating exposed to a mildly corrosive electrolyte solution can be obtained if the transfer coefficients and exchange current densities are known for the reactions occurring on the two metals. These parameters can be determined from measurements of current as a function of electrode potential for the anodic substrate dissolution process and for the cathodic process (oxygen or proton reduction, for example) occurring on the coating metal. Alternatively, potential measurements can be calibrated in terms of the coating/substrate area ratio by measuring the potential difference between specimens of the coating and substrate metals having known areas. Typically, the area of the coating specimen is held constant while that of the substrate specimen is varied. For the particular electrolyte (0.1M $NH_4Cl$) and stagnant solution used by Morrissey, long times of 10 to 100 minutes were required to reach a steady-state potential. Experiments recently performed by Applicants suggest that potential measurements made using stagnant electrolytes do not provide an accurate measure of coating porosity in most cases.

Because of the limitations of the prior art, there is a need for a rapid, practical, and quantitative method for determining porosity of protective coatings and oxidation of the underlying substrate. Such a method would lead to improvements in coating processes and quality control. It would be particularly beneficial for evaluating protective coatings, such as gold, palladium, or organic coatings on nickel or copper, that are used in the electronics and jewelry industries.

SUMMARY OF THE INVENTION

The method of the present invention is termed Potentiometric Evaluation of Substrate Oxidation ("PESO"). It is useful for evaluating the quality of protective coatings by providing a quantitative measure of both coating porosity and substrate oxidation. The method is fast, nondestructive, and easy to perform.

In the method of the present invention, a coated part to be analyzed is placed in contact with an electrolytic solution having a pH adjusted to provide an optimum oxide dissolution rate. The open circuit potential of the part is monitored, usually relative to a reference electrode, as the substrate oxides dissolve in the electrolytic solution. The voltage typically changes as a function of time during oxide dissolution. When oxide dissolution is complete, the voltage reaches a steady value associated with active dissolution of the substrate metal and reduction processes occurring on the surface of the protective coating. Flowing or agitating the electrolytic solution can reduce concentration polarization, provide more meaningful voltage measurements, and minimize the time required to reach a steady-state voltage. The time required to reach a steady-state voltage provides a measure of the amount of substrate oxides within pores in the coating, which relates to solderability of electronic parts. The final steady-state voltage level provides a measure of the relative areas of the coating and the exposed substrate, which relates to the porosity of the coating.

A principal object of the invention is evaluation of substrate oxidation associated with coating porosity. A feature of the invention is potentiometric evaluation of a coated part in contact with an electrolytic solution. An advantage of the invention is a method of evaluating properties of protective coatings (including solderability) that is fast, nondestructive, and easy to perform.

BRIEF DESCRIPTION OF THE DRAWINGS

For a more complete understanding of the present invention and for further advantages thereof, the following Detailed Description of the Preferred Embodiments makes reference to the accompanying Drawings, in which.

DETAILED DESCRIPTION OF THE PREFERRED EMBODIMENTS

Figure 1:
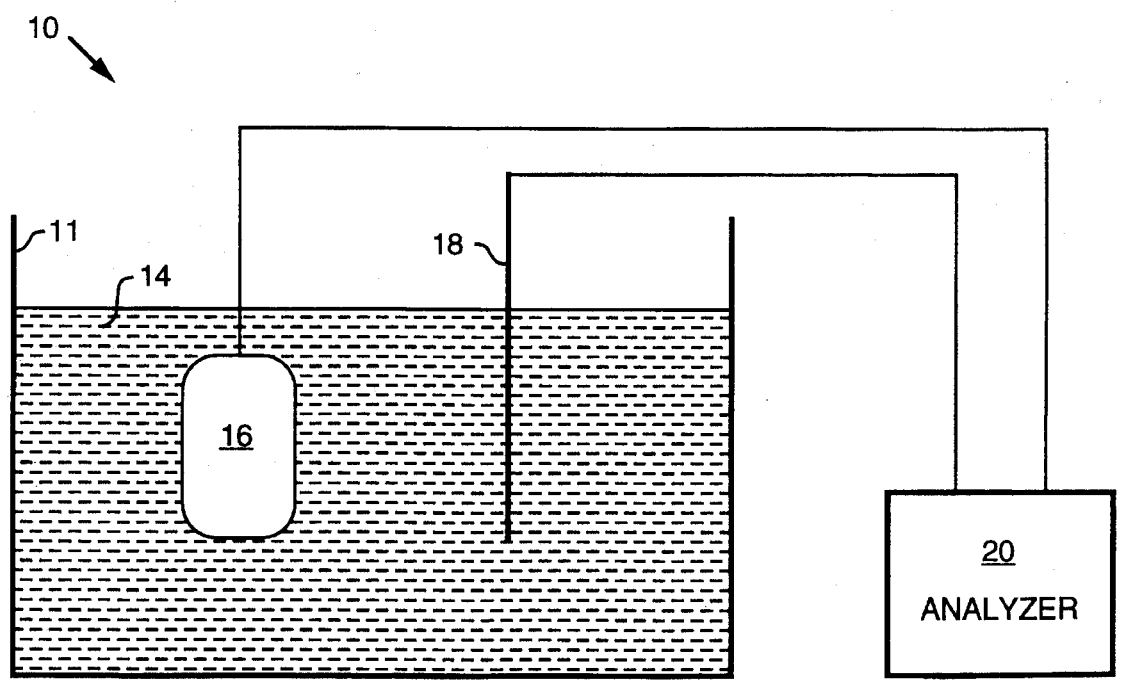
FIG. 1 is a schematic diagram of a simplified apparatus for performing the present method of potentiometric evaluation of substrate oxidation and coating porosity.

The method of the present invention, which is termed Potentiometric Evaluation of Substrate Oxidation ("PESO"), is useful for evaluating noble metal coatings, such as gold or palladium on nickel or copper, and organic solderability preservative (OSP) coatings, such as benzotriazole and various imidazoles on copper substrates, for example. In some cases, the method may also be useful for evaluating oxidation of uncoated metal surfaces (for solderability assessment, for example). The basic components of an apparatus 10 for performing the PESO method are illustrated schematically in FIG. 1. Apparatus 10 includes a reservoir 11 for containing an electrolytic solution 14. A part 16 (or a selected portion of part 16) having a protective coating to be evaluated is placed in contact with electrolytic solution 14. Typically, a reference electrode 18, which may comprise a saturated calomel electrode (SCE), for example, is also placed in contact with electrolytic solution 14. Part 16 and reference electrode 18 are connected electrically to an analyzer 20 that may comprise an electrical meter (e.g., a volt meter), typically in combination with a monitor, a recorder, and/or a computer processor, for example.

Electrolytic solution 14 is selected, and its pH is adjusted, to provide an optimum dissolution rate for substrate oxides that exist in pores of the coating on part 16. Electrolytic solution 14 is formulated to dissolve oxides slowly enough to minimize concentration polarization (avoiding voltage errors) associated with buildup of dissolved species within coating pores, but rapidly enough for fast analysis. Enhanced solution mass transport may be provided by flowing or agitating solution 14, or moving part 16 relative to solution 14, for example. Solution mass transport greatly reduces concentration polarization so that more meaningful voltage measurements can be obtained and the time required to reach a steady-state voltage can be minimized. For best results, the pH of solution 14 should be maintained constant (with an appropriate buffer, for example), and the solution mass transport should be reproducibly controlled (by flowing the solution at a constant rate, for example) so that the dissolution rate for a particular type of substrate oxide is constant. Deoxygenation of solution 14 generally is not necessary, but may be desirable in some potentiometric evaluations.

Using the method of the present invention, the open circuit potential of part 16 is monitored by analyzer 20 (usually at regular intervals relative to reference electrode 18) as substrate oxides of part 16 dissolve in electrolytic solution 14. The voltage measured by analyzer 20 typically changes as a function of time during oxide dissolution. After oxide dissolution is complete, the measured voltage reaches a steady value (corrosion potential) associated with active dissolution of the substrate metal and reduction processes on the surface of the coating (usually reduction of oxygen or protons). The time required to reach a steady-state voltage provides a relative measure of the amount of substrate oxide within pores of the coating on part 16. This can be calibrated by analyzer 20 to provide an absolute measure of the substrate oxide thickness (and a corresponding measure of solderability of part 16). The final steady-state voltage level reflects the relative areas of the coating and the exposed substrate, which relate to the porosity of the coating on part 16. Thus, the steady-state voltage under well-defined hydrodynamic conditions provides an accurate measure of the coating porosity. It is anticipated that voltage transients recorded during oxide dissolution will provide information as to the nature of the oxide(s) present. For example, rapid dissolution of the more easily dissolved oxides may produce a rapid change in electrode potential, which may be followed by a slower change in potential if less easily dissolved oxides are present. Such data can be correlated with solderability of part 16, as further described in U.S. Pat. No. 5,262,022, the teachings of which are hereby incorporated by reference.

TEST RESULTS

PESO measurements were made using a Solder Scan QC-100 (SERA Solderability Tester) manufactured by ECI Technology, Inc., East Rutherford, N.J. Test specimens 16 consisted of copper foil or printed wiring board (PWB) coupons having electroless nickel finishes coated with immersion gold (Lea Ronal Ronamerse SMT Process). The Solder Scan QC-100, which is designed for sequential electrochemical reduction analysis (SERA), as described in U.S. Pat. No. 5,262,022, uses an O-ring gasket to isolate a 2.0 $mm^2$ area for analysis. Electrolytic solution 14 was pumped over this area at a rate of 120 mL/minute (using the "pad mode" of the Solder Scan QC-100). Electrolyte 14 was a nitrogen-saturated acetate buffer at pH 4.0 and an acetate concentration of approximately 1.2M (57.5 mL/L glacial acetic acid and 23.8 g/L sodium acetate trihydrate).

Figure 2:
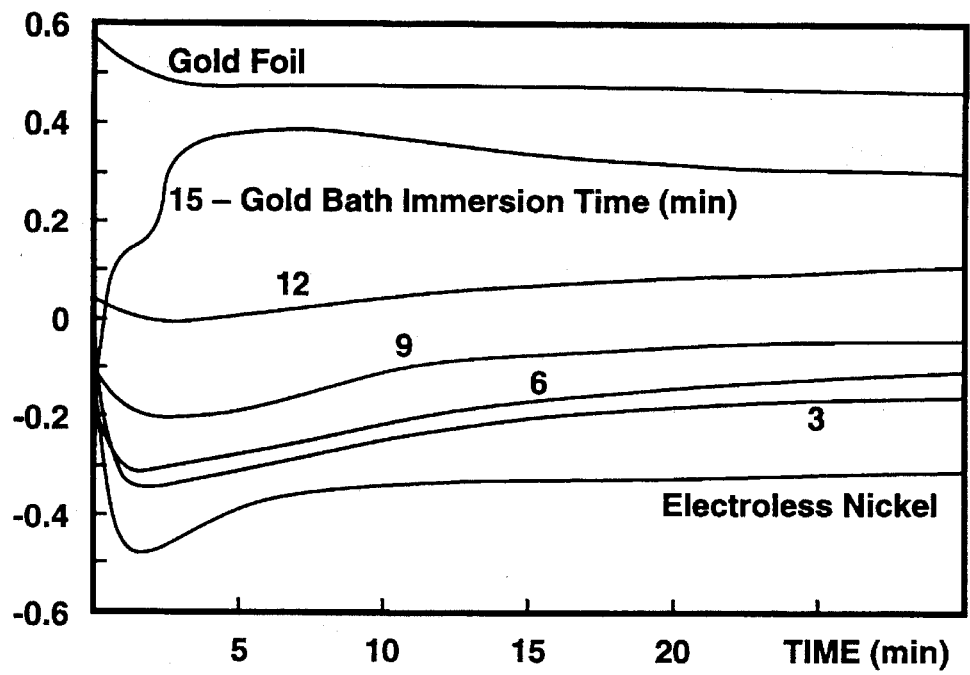
FIG. 2 is a graphical plot of electrode potential (volts versus SCE reference electrode) versus time in contact with an electrolyte comparing gold foil to electroless nickel on copper foil coated by gold bath immersion for various periods of time.

FIG. 2 shows potentiometric evaluation curves generated for gold foil, electroless nickel (on copper foil), and electroless nickel substrates coated with immersion gold. The gold coated substrates are compared as a function of increasing immersion time in the gold bath (3, 6, 9, 12, and 15 minutes, respectively), which reduces the porosity of the gold coating. The standard immersion time is 15 minutes, so that most of the specimens were atypical, having very thin gold coatings with high porosities. Nonetheless, relatively steady voltages were attained, which tracked the gold coating porosity (a function of the immersion bath time). Because these specimens were not aged, the time to reach a stable potential was short, indicating relatively little substrate oxidation.

Figure 3:
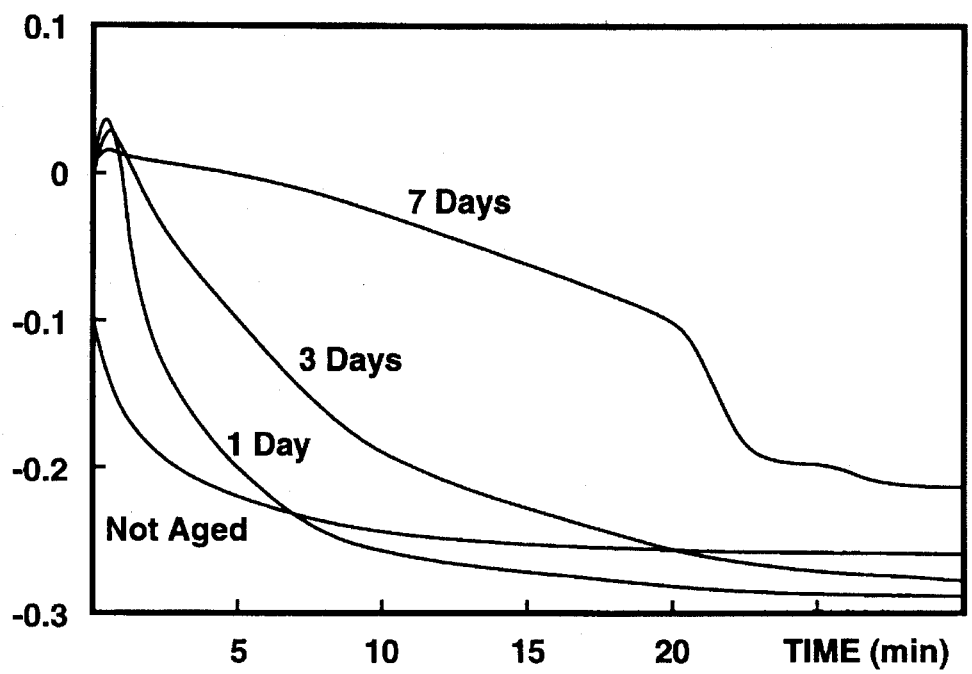
FIG. 3 is a graphical plot of electrode potential (volts versus SCE reference electrode) versus time in contact with an electrolyte comparing standard immersion gold/electroless nickel coatings on PWB coupons after various aging times at 65° C. and 85% relative humidity.

FIG. 3 shows potentiometric evaluation curves for standard immersion gold/electroless nickel coatings on PWB coupons as a function of aging time at 65° C. and 85% relative humidity. The data plotted in FIG. 3 illustrate the efficacy of the method of the present invention for detecting substrate oxidation. During dissolution of the nickel substrate oxide, the voltage is shifted to more positive values, producing an ill-defined voltage-time wave. With increasing aging time, this wave becomes longer, reflecting increased substrate oxidation. Even for the specimen aged for 7 days, a steady voltage is attained within about 25 minutes. As expected, the final voltage is approximately constant for these initially equivalent specimens, indicating that the gold coating had approximately the same porosity in each specimen. The somewhat higher final voltage for the specimen aged 7 days may reflect decreased porosity for this specimen or formation of an oxide that dissolved only slowly in the electrolytic solution used. Comparable results have also been obtained for PESO analysis of palladium coatings on both copper and nickel substrates using the same pH 4.0 acetate electrolyte described above.

Although the present invention has been described with respect to specific embodiments thereof, various changes and modifications can be carried out by those skilled in the art without departing from the scope of the invention. Therefore, it is intended that the present invention encompass such changes and modifications as fall within the scope of the appended claims.

We claim:

1. A method of determining oxidation of a substrate having a coating, comprising the steps of:

placing the coated substrate in contact with an electrolytic solution, said solution for dissolving oxides of said substrate;

placing a reference electrode in contact with said solution;

measuring open circuit potential of said coated substrate with respect to said reference electrode while in contact with said solution; and measuring time for said open circuit potential to reach a steady-state voltage to determine oxidation of said substrate.

2. The method of claim 1, further comprising the step of connecting said coated substrate and said reference electrode to a means for measuring said open circuit potential.

3. The method of claim 2, wherein said placing steps comprise placing said coated substrate and said reference electrode in contact with an acetate buffer solution, and adjusting pH of said acetate buffer solution for dissolution of said oxides of said substrate.

4. The method of claim 1, further comprising the step of correlating said oxidation of said substrate with solderability of said coated substrate.

5. The method of claim 1, further comprising the step of providing controlled mass transport of said solution to reduce concentration polarization.

6. The method of claim 5, further comprising the step of measuring said steady-state voltage to determine relative areas of said coating and said substrate exposed to said electrolytic solution, which relate to porosity of said coating.

7. The method of claim 6, further comprising the step of correlating said relative areas of said coating and said substrate to determine porosity of said coating.

8. A method of evaluating a coating on a substrate by determining oxidation of the substrate, comprising the steps of:

placing the coated substrate in contact with an electrolytic solution, said solution for dissolving oxides of said substrate;

placing a reference electrode in contact with said solution;

connecting said coated substrate and said reference electrode to a means for measuring electrical potential;

measuring open circuit potential between said coated substrate and said reference electrode in contact with said solution; and measuring time for said open circuit potential to reach a steady-state voltage to determine oxidation of said substrate.

9. The method of claim 8, further comprising the step of measuring said steady-state voltage to determine relative areas of said coating and said substrate exposed to said electrolytic solution, which relate to porosity of said coating.

10. The method of claim 9, further comprising the step of correlating said relative areas of said coating and said substrate to determine porosity of said coating.

11. The method of claim 8, wherein said placing steps comprise placing said coated substrate and said reference electrode in contact with an acetate buffer solution, and adjusting pH of said acetate buffer solution for dissolution of said oxides of said substrate.

12. The method of claim 8, further comprising the step of correlating said oxidation of said substrate with solderability of said coated substrate.

13. The method of claim 8, further comprising the step of providing controlled mass transport of said solution to reduce concentration polarization.

14. The method of claim 8, wherein the step of measuring said open circuit potential comprises measuring said open circuit potential at regular intervals during dissolution of said oxides of said substrate.

15. A method of determining porosity of a protective coating on a substrate and oxidation of the substrate, comprising the steps of:

placing the coated substrate in contact with an electrolytic solution, said solution for dissolving oxides of said substrate;

placing a reference electrode in contact with said solution;

connecting the coated substrate and said reference electrode to an electrical analyzer;

measuring open circuit potential between said coated substrate and said reference electrode in contact with said solution;

measuring time for said open circuit potential to reach a steady-state voltage to determine oxidation of the substrate; and measuring said steady-state voltage to determine relative areas of the coating and the substrate exposed to said electrolytic solution, which relate to porosity of said coating.

16. The method of claim 15, wherein said placing steps comprise placing the coated substrate and said reference electrode in contact with an acetate buffer solution, and adjusting pH of said acetate buffer solution for dissolution of said oxides of said substrate.

17. The method of claim 15, further comprising the step of correlating said oxidation of said substrate with solderability of said coated substrate.

18. The method of claim 15, further comprising the step of providing controlled mass transport of said solution to reduce concentration polarization.

19. The method of claim 15, further comprising the step of correlating said relative areas of the coating and the substrate to determine porosity of the coating.

20. The method of claim 15, wherein the step of measuring said open circuit potential comprising measuring said open circuit potential at regular intervals during dissolution of said oxides of the substrate.

* * * * *